United States Patent
Blatter et al.

(10) Patent No.: US 8,916,559 B2
(45) Date of Patent: Dec. 23, 2014

(54) CRYSTALLINE COMPOUND OF 7-[(3R)-3-AMINO-1-OXO-4-(2, 4, 5-TRIFLUOROPHENYL)BUTYL]-5, 6, 7, 8-TETRAHYDRO-3-(TRI FLUOROMETHYL)-1, 2, 4-TRIAZOLO[4,3-A]PYRAZIN

(75) Inventors: Fritz Blatter, Reinach (CH); Katharina Reichenbächer, Riehen (CH)

(73) Assignee: Sandoz AG, Basel (CH)

( * ) Notice: Subject to any disclaimer, the term of this patent is extended or adjusted under 35 U.S.C. 154(b) by 158 days.

(21) Appl. No.: 13/390,039

(22) PCT Filed: Aug. 12, 2010

(86) PCT No.: PCT/EP2010/061733
§ 371 (c)(1),
(2), (4) Date: Feb. 10, 2012

(87) PCT Pub. No.: WO2011/018494
PCT Pub. Date: Feb. 17, 2011

(65) Prior Publication Data
US 2012/0142693 A1   Jun. 7, 2012

(30) Foreign Application Priority Data
Aug. 13, 2009 (EP) .................................... 09167825

(51) Int. Cl.
*C07D 487/04*   (2006.01)
*A61K 31/4985*   (2006.01)

(52) U.S. Cl.
CPC .................................... *C07D 487/04* (2013.01)
USPC .......................................... 514/249; 544/350

(58) Field of Classification Search
None
See application file for complete search history.

(56) References Cited

U.S. PATENT DOCUMENTS 8,329,696 B2 * 12/2012 Pilarski et al. ................ 514/249

FOREIGN PATENT DOCUMENTS

| WO | WO 03/004498 A | 1/2003 |
| WO | WO 2005/003135 A | 1/2005 |
| WO | WO 2005/072530 A | 8/2005 |
| WO | WO 2009/085990 A | 7/2007 |
| WO | 2010/000469 A2 * | 1/2010 |

OTHER PUBLICATIONS

Kakkar et el. Drug Development and Industrial Pharmacy, vol. 23(11), pp. 1063-1067 (1997).*
M.R. Caira, "Crystalline Polymorphism of Organic Compounds", Topics in Current Chemistry, Jan. 1998, vol. 198, pp. 163-208.
Dooseop Kim et al., "(2R-4-Oxo-4[3-(Trifluoromrthyl)-5,6-dihydro[1,2,4]triazolo[4,3-a]pyrazin7(8H)-yl]-1-(2,4,5-tryfluorophenyl)butan-2-amine: A Potent, orally Active Dipeptidyl Peptidase IV Inhibitor for the Treatment of Type 2 Diabetes", Journal of Medicinal Chemistry, Jan. 2005, vol. 48, No. 1, pp. 141-151.

* cited by examiner

*Primary Examiner* — Emily Bernhardt
(74) *Attorney, Agent, or Firm* — Arent Fox LLP

(57) ABSTRACT

A crystalline compound of 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine (INN: Sitagliptin) of formula 1

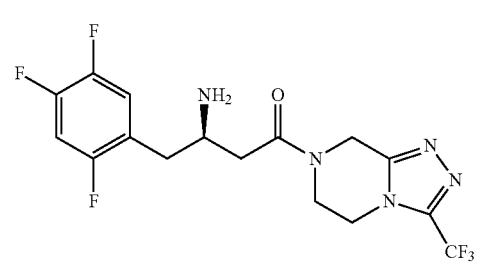

formula 1 with fumaric acid or a hydrate thereof, where the molar ratio of the compound of formula 1 to fumaric acid is 1:0.6 to 1:1.3 is described.

7 Claims, 4 Drawing Sheets

Powder diffractogram of form A

CRYSTALLINE COMPOUND OF 7-[(3R)-3-AMINO-1-OXO-4-(2, 4, 5-TRIFLUOROPHENYL)BUTYL]-5, 6, 7, 8-TETRAHYDRO-3-(TRI FLUOROMETHYL)-1, 2, 4-TRIAZOLO[4,3-A]PYRAZIN

CROSS-REFERENCE TO RELATED APPLICATION

This application is a National Stage entry of International Application No. PCT/EP2010/061733, filed Aug. 12, 2010, which claims priority to Application No. EP No. 09167825.0, filed Aug. 13, 2009, the entire specifications, claims and drawings of which are incorporated herewith by reference.

The present invention relates to a crystalline compound of 7-[(3R)-3-amino-1-oxo-4-(2,4,5-trifluoro phenyl)butyl]-5,6,7,8-tetrahydro-3-(trifluoromethyl)-1,2,4-triazolo[4,3-a]-pyrazine (INN: Sitagliptin) with fumaric acid or a hydrate thereof. The present invention further provides a process for the production thereof.

BACKGROUND OF THE INVENTION

Diabetes refers to a disease process which stems from a number of causal factors and is evident from increased plasma glucose levels or hyperglycemia during the fasting state or following the administration of glucose during an oral glucose tolerance test. Persistent or uncontrolled hyperglycemia is associated with an increased and premature morbidity and mortality. An abnormal glucose homeostasis is often associated both directly and indirectly with changes in the lipid, lipoprotein and apolipoprotein metabolism and with other metabolic and hemodynamic diseases. Consequently, for patients with type 2 diabetes mellitus, there is a particularly high risk of macrovascular and microvascular complications, including coronary heart disease, apoplexy, peripheral vascular disease, hypertension, nephropathy, neuropathy and retinopathy. The therapeutic control of glucose homeostasis, lipid metabolism and hypertension is of decisive importance for the clinical handling and treatment of diabetes mellitus.

There are two generally recognized forms of diabetes. In type 1 diabetes or insulin-dependent diabetes mellitus (IDDM), the patients produce little or no insulin, a hormone which controls the glucose utilization. In type 2 diabetes or non-insulin-dependent diabetes mellitus (NIDDM), the patients often have plasma insulin levels which correspond to or are even higher than those of non-diabetic patients. However, these patients have developed a resistance to the insulin-stimulating effect on the glucose and lipid metabolism in the large insulin-sensitive tissues, which are muscle, liver and fatty tissue, and the plasma insulin levels, although increased, are insufficient for overcoming the marked insulin resistance.

Insulin resistance is not primarily the result of a reduced number of insulin receptors, but the result of a post insulin receptor binding defect which has still not been explained. This resistance to insulin sensitivity leads to inadequate insulin activation of the glucose absorption, oxidation and storage in the muscle and to inadequate insulin suppression of lipolysis in fatty tissue and the production and secretion of glucose in the liver.

It has been found that there are a large number of compound classes which can be used for the treatment of diabetes. Those worthy of particular mention here are the inhibitors of the dipeptidylpeptidase-IV enzyme ("DP-IV inhibitors") which are suitable for the treatment or prevention of diseases in which the dipeptidylpeptidase-IV enzyme is involved, such as e.g. diabetes and in particular type 2 diabetes.

WO 03/004498 A1 proposes as such DP-IV inhibitors substances with a pyrazine structure, among which 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine (INN: Sitagliptin) is also mentioned. In particular, a sitagliptin hydrochloride is also described. This hydrochloride is hygroscopic.

In WO 2005/003135 describes a sitagliptin dihydrogenphosphate salt which has evidently been obtained as hydrate but is phase-unstable at temperatures above 40° C. This implies that the production of relatively large amounts on an industrial scale leads to a drying process that is difficult to control.

WO 2005/072530 A1 discloses further salts of sitagliptin. These compounds too are said to be used as DP-IV inhibitors for treating diabetes. Neither WO 03/004498 A1 nor WO 2005/072530 A1 discloses compounds comprising sitagliptin and fumaric acid.

Kim et al., J. Med. Chem. 2005, 48, 141-151 have investigated orally active DP-IV inhibitors for treating type 2 diabetes. Inter alia, sitagliptin is reacted with fumaric acid for an in vivo investigation. In this process, a solid is obtained in which the ratio of sitagliptin to fumaric acid is 1:0.5. A characterization takes place only by means of NMR and HRMS. It is not stated whether the resulting solid is crystalline.

In the prior art, there is the need to provide compounds comprising sitagliptin which allow improved administration. In particular, the aim is to provide an administration form of sitagliptin which takes into consideration the requirements of the pharmacokinetics of the active ingredient and moreover can be used in the formulation of an oral administration form. In particular, the aim is to provide a compound which has an optimized low water absorption upon storage.

BRIEF SUMMARY OF THE INVENTION

The technical object of the present invention is achieved by a crystalline compound of 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine (INN: Sitagliptin) of formula 1 formula 1

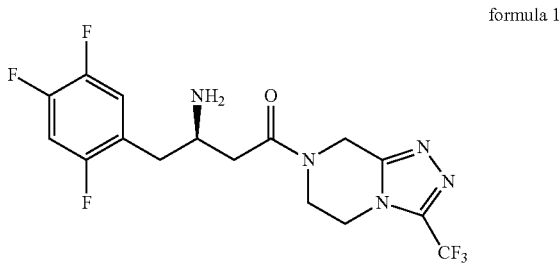 [SMILES: N[C@@H](CC(=O)N1CCn2c(nnc2C(F)(F)F)C1)Cc1cc(F)c(F)cc1F]

with fumaric acid or a hydrate thereof, where the molar ratio of the compound of formula 1 to fumaric acid is 1:0.6 to 1:1.3.

Surprisingly, fumaric acid and sitagliptin form a crystalline compound having the aforementioned molar ratio of sitagliptin to fumaric acid. This was not foreseeable by the person skilled in the art from the prior art since he had to assume that sitagliptin and fumaric acid do not form crystalline compounds.

DETAILED DESCRIPTION OF THE INVENTION

Figure 1:
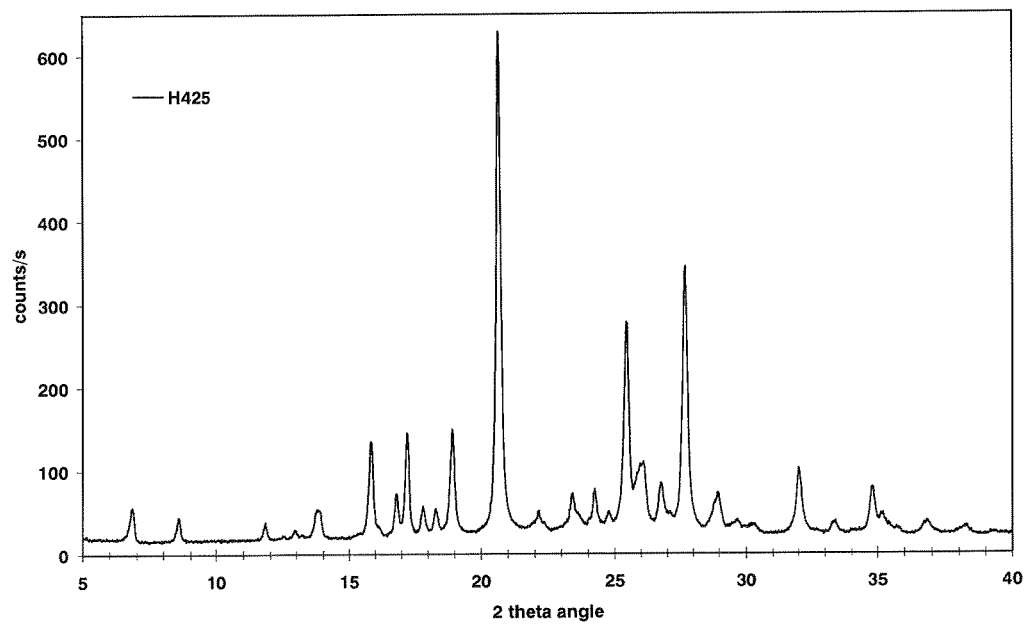
FIG. 1 is a powder diffractogram of form A.

Amorphous forms are generally characterized in that these do not exhibit sharp powder diffraction reflections. The powder diagram of amorphous forms has merely a greatly increased background signal in the °2θ range from ca. 10° to 30°.

Mesomorphic forms are normally characterized in that these have only very few, often only one or two, or even no, sharp powder diffraction reflections. Mixtures of amorphous and crystalline phases in particular have only very weak powder diffraction reflections when the amorphous fraction is very high; for example 50% or higher.

X-ray powder diffraction is a widespread and widely recognized method for identifying and characterizing molecular bodies. Descriptions of this method can be found both in the European Pharmacopoeia and also in the US Pharmacopeia as Method No. 941 "X-Ray Diffraction", or in "Polymorphism—In the Pharmaceutical Industry" Chapter 6, Rolf Hilfiker, Editor Wiley-VCH Verlag, Weinheim, Germany, 2006. Normally, X-ray powder diffraction is carried out with copper-$K_\alpha$ radiation, as was also the case here. D values in Å (d) and 2-theta (2θ) values in angle-degree can be converted to one another by Bragg's equation as follows: $n\lambda = 2d \sin \theta$, where n is an integer and λ is the wavelength of the X-ray radiation used in Å. The data obtained from a powder diffraction measurement are signal intensity (in counts) as a function of the angle 2θ. Moreover, it is to be taken into consideration that measurement can be made both in reflection geometry and also in transmission geometry. The measurements mentioned here were carried out in reflection geometry. Whereas the position of the lines in angle-degree is not dependent on the geometry, the relative intensities, however, can change both as a result of the geometry and also as a result of the properties of the sample and as a result of the sample preparation. Consequently, the stated intensities serve merely as a qualitative feature. For measurements of this kind, the measurement error is usually ±0.1° 2θ. Whereas the measurement error for °2θ changes only slightly, if at all, over the entire measurement range, on account of the aforementioned Bragg's equation, the error in the case of the d values is dependent on the angle. However, 2θ angles and d values are equivalent and therefore no measurement error has been calculated for the d values although one is present.

A particular feature of the invention present here is crystalline compounds of sitagliptin with fumaric acid which are distinguished by a high crystalline purity. This is characterized in that the powder X-ray diagrams of these compounds have at least four peaks, each of which preferably has a signal to noise ratio of at least 4. Further preferred is a signal to noise ratio of at least 8 or higher, where the X-ray powder diffraction measurements are to be carried out under the measurement conditions described here or equivalent measurement conditions.

Compared to the known prior art, with regard to compounds comprising fumaric acid, the crystalline compound according to this invention preferably has a large number and sharp powder diffraction reflections.

Raman spectroscopy is a second very useful method for identifying and characterizing various forms of molecular bodies. Detailed descriptions of the use of Raman spectroscopy for the mentioned purpose can be found e.g. in "Polymorphism—In the Pharmaceutical Industry" Chapter 5, Rolf Hilfiker, Editor Wiley-VCH Verlag, Weinheim, Germany, 2006. For measurements of this kind, the measurement error is usually +1 $cm^{-1}$.

In a preferred embodiment, the crystalline compound has, by means of X-ray powder diffractometry (XRPD), d values (Å) at 12.9 (w), 10.3 (w), 5.15 (m) and 4.30 (vs), which is subsequently referred to as form A. Further preferably, the compound (form A) has, by means of X-ray powder diffractometry (XRPD) d values (Å) at 12.9 (w), 10.3 (w), 5.15 (m), 4.69 (m), 4.30 (vs), 3.50 (s), 3.22 (s). FIG. 1 shows a powder diffractogram of form A.

The molar ratio of the compound of formula 1 to fumaric acid is preferably 1:0.95 to 1:1.05, where this ratio is preferably present in the case of form A.

Form A preferably has characteristic Raman bands at 3083, 3034, 3019, 2940, 1707, 1655, 1516, 1479, 1439, 1389, 1338, 1260, 979, 899, 807, 756, 748, 697, 537, 453, 396, 288, 213, 104 and 85 $cm^{-1}$ (wave numbers). The more intense Raman bands of form A are found preferably at 3034, 2940, 1655, 1516, 756 and 104 $cm^{-1}$ (wave numbers).

Amorphous or mesomorphous forms of a compound can have a very much stronger tendency toward hygroscopicity than crystalline forms. The sitagliptin fumarate compounds described here are characterized in that they have good hygroscopic properties, i.e. absorb little water at high relative humidity. This is evident from table 1 below, which compares the water contents of the crystalline fumarate form A and crystalline hydrochloride at 50% and 90% relative humidity. The data originate from dynamic water vapor adsorption measurements. The water vapor sorption measurement is a suitable method for investigating the hygroscopic properties of solid substances. Water vapor sorption measurements can be carried out in different ways. In general, in this connection, a small sample of ca. 10-30 mg is introduced into a microbalance in a suitable sample carrier. The sample is then exposed to different relative humidities in accordance with a defined program, the change in the sample mass being simultaneously recorded over the time. As a result, insights into the hygroscopic behavior of a substance can be obtained. Both crystalline sitagliptin hydrochloride monohydrate and also crystalline compounds of the present invention were investigated using this method and it was established that the hydrochloride adsorbs significantly more water under identical measurement conditions and is thus more hygroscopic. It has been found that for example crystalline fumarate in form A at 50% relative humidity contains only ca. 0.3% water, and after four hours at 96% relative humidity absorbs only just ca. 1% more water than at 50% relative humidity, the latter value corresponding approximately to the standard humidity conditions in central Europe.

TABLE 1

Results of the water vapor sorption measurements

| Salt form | $H_2O$ content at 50% r.h. | $H_2O$ content at 90% r.h. |
| --- | --- | --- |
| Crystalline sitagliptin fumarate form A | 0.25% | 1.33% |
| Crystalline sitagliptin hydrochloride according to prior art | >2.7% | >3.6% |

This result is unexpected for the person skilled in the art and cannot be deduced from the prior art. Consequently, the crystalline compounds of the present invention offer a profile of properties which is advantageous for use in medicaments.

Figure 2:
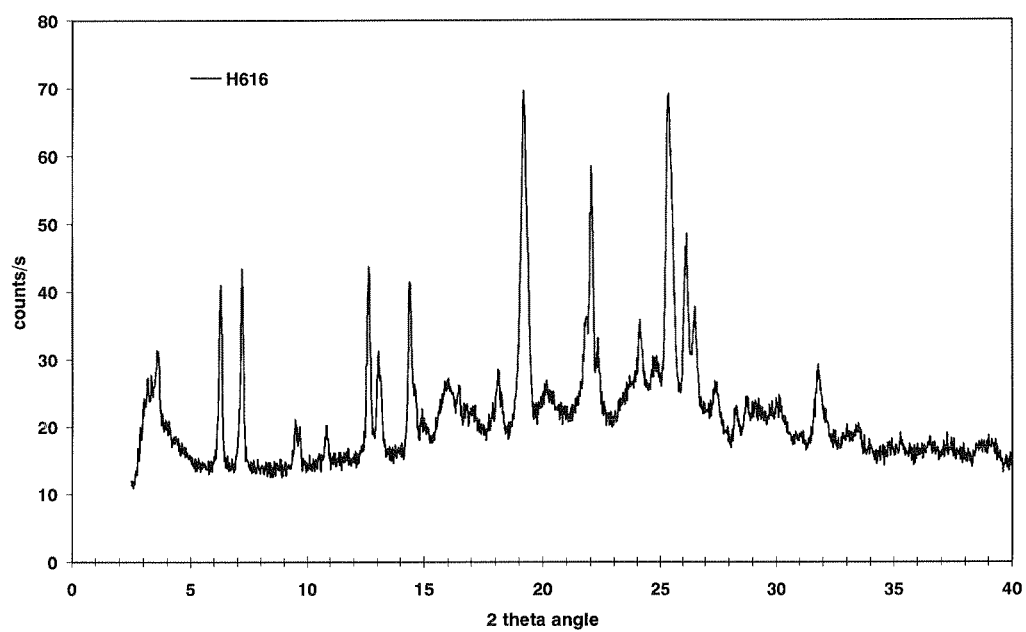
FIG. 2 is a powder diffractogram of form B.

In a further embodiment, the crystalline compound has, by means of X-ray powder diffractometry (XRPD), d values (Å) at 12.3 (s), 7.0 (s), 4.62 (vs) and 3.51 (vs), which is subsequently referred to as form B. Further preferably the compound (form B) has, by means of X-ray powder diffractometry (XRPD), d values at 14.1 (s), 12.3 (s), 7.0 (s), 6.1 (s), 4.62 (vs), 4.03 (vs) and 3.51 (vs). FIG. 2 shows a powder diffractogram of form B.

Figure 3:
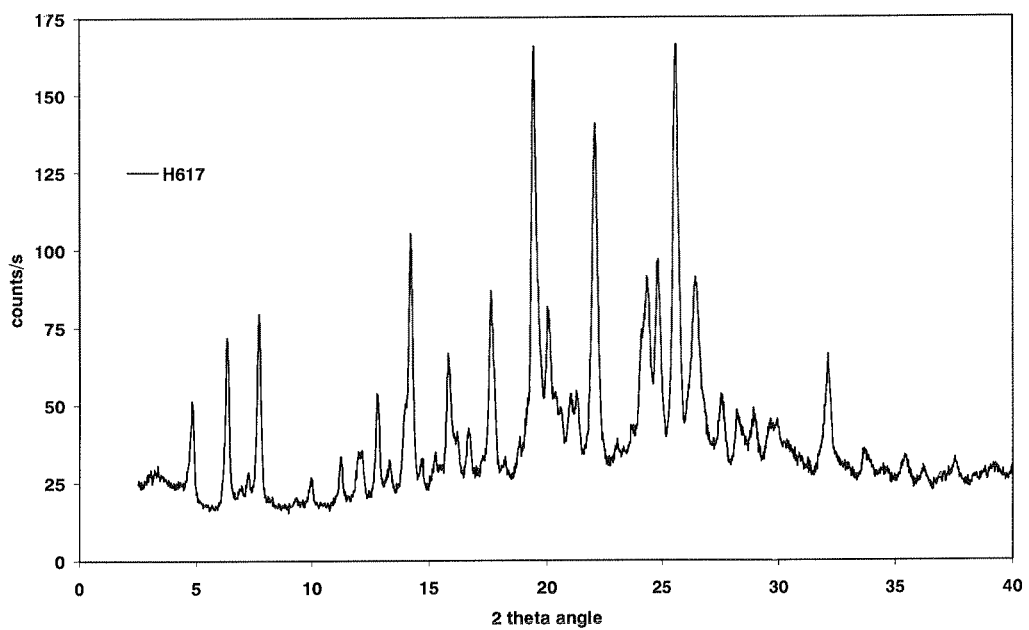
FIG. 3 is a powder diffractogram of form C.

In a further preferred embodiment, the compound has, by means of X-ray powder diffractometry (XRPD), d values (Å) at 18.3 (m), 11.4 (s), 4.56 (vs) and 3.47 (vs), which is subsequently referred to as form C. Further preferably the compound (form C) has, by means of X-ray powder diffractometry (XRPD), d values at 18.3 (m), 13.9 (s), 12.2 (w), 11.4 (s), 6.2 (s), 5.02 (m), 4.56 (vs), 4.03 (vs) and 3.47 (vs). FIG. 3 shows a powder diffractogram of form C.

The molar ratio of the compound of formula 1 to fumaric acid is preferably 1:0.60 to 1:0.80, where this ratio is present preferably in the case of form B and/or C.

The present invention further provides a medicament comprising the crystalline compound.

The crystalline compound is preferably used for treating diabetes.

The present invention further provides a method for producing the crystalline compound.

The method involves the steps:
a) provision of a solution of 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine (INN: Sitagliptin) of formula 1,
b) addition of fumaric acid to the solution in step a),
c) optional concentration of the composition obtained after step b) and/or optional addition of a suitable non-solvent for lowering the solubility of the crystalline compound, and
d) removal and subsequent drying of the solid obtained.

Preferably, the fumaric acid in step b) can be added as solid to the solution in step a). Alternatively, the fumaric acid in step b) can be added as a solution in a suitable solvent to the solution in step a). In a further preferred embodiment, it is also possible to swap steps a) and b), i.e. the solution in step a) comprising sitagliptin is added to fumaric acid in step b).

Preferably, the solvent in step a) and/or optional solvent in step b) is in each case an organic or inorganic solvent.

In a preferred embodiment, the molar ratio of the dissolved compound of formula 1 in step a) to the fumaric acid in step b) is 1:0.6 to 1:1.3.

It is further preferred that, for producing form A, the molar ratio of the dissolved compound of formula 1 in step a) to the fumaric acid in step b) is 1:0.90 to 1:1.10 and further preferably 1:0.95 to 1:1.05.

It is moreover preferred that, for producing form B or C, the molar ratio of the dissolved compound of formula 1 in step a) to the fumaric acid in step b) is 1:0.60 to 1:0.80.

Further preferably, low molecular weight and physiologically compatible solvents and/or physiologically compatible alcohols, such as e.g. ethanol, isopropanol, 1-propanol, n-butanol, low molecular weight ketones, such as e.g. acetone, 2-butanone, methyl isobutyl ketone, acetates, e.g. ethyl formate, ethyl acetate, butyl acetate or isopropyl acetate or ethers, e.g. tert-butyl methyl ether, diethyl ether, diisopropyl ether or mixtures thereof to be combined as desired are used for step a) and/or step b). For step a) and/or step b), particular preference is given to physiologically compatible solvents in which the fumaric acid is soluble to an adequate extent. Preference is given to ethanol, 1-propanol, 2-propanol, THF, acetone, ethyl methyl ketone, water and mixtures thereof. Particular preference is given for step a) to ethanol, 2-propanol, ethyl acetate, isopropyl acetate, acetone, ethyl methyl ketone and for step b) ethanol, 2-propanol, acetone, ethyl methyl ketone and water.

"Physiologically compatible" means that these solvents fall under the ICH (International Commission for Harmonization) guideline Q3C, Class 3. The order of steps a) and b) can be swapped.

In steps a) and b), the two components can be dissolved either in the same solvent or in different solvents, and either in identical concentrations or in different concentrations. It is also possible to use in each case solvent mixture of two or more solvents in step a) and/or step b).

Alternatively, it is preferred to use a compound of 7-[(3R)-3-amino-1-oxo-4-(2,4,5-trifluorophenyl)butyl]-5,6,7,8-tetrahydro-3-(trifluoromethyl)-1,2,4-triazolo[4,3-a]-pyrazine (INN: Sitagliptin) of formula 1

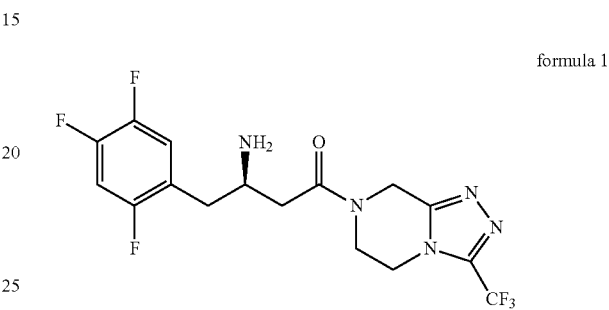

formula 1 with fumaric acid or a hydrate thereof as starting material for the crystallization.

In step c), preferably seed crystals of the desired form can be added. In step c), it is further preferred that the resulting suspension is stirred at a suitable temperature. Preferably, this temperature is in the range from 5° C. to 50° C.

Furthermore, in steps a) and b), the crystallization temperature, or the attainment of the saturation with regard to the desired salt can be modulated through the choice of different combinations of the solvents and concentrations in such a way that the desired salt is obtained in high yield and high purity.

To produce form A, sitagliptin and fumaric acid is preferably stirred into 2-butanone (methyl ethyl ketone) or acetonitrile. The molar ratio of sitagliptin to fumaric acid here is preferably 1:1±0.1. Preferably, the composition is stirred for at least one day at preferably room temperature. In a further preferred embodiment, the solvent is evaporated at least partially during stirring.

A further preferred embodiment for producing form B involves the recrystallization of form A from a solvent mixture of ethanol and ethyl acetate.

Preferably, form B can be obtained by stirring form A as a slurry in a mixture of ethanol and water. Preferably, the slurry is stirred for at least one day at preferably room temperature.

A further preferred embodiment for producing form C involves the recrystallization of form A from the solvent 2-propanol.

Surprisingly, form A can be used as starting material for producing other forms, such as form B or form C of the crystalline compound of the present invention. Form A is obtainable in high purity. In this connection, form A of the present invention is preferably introduced as initial charge in a suitable solvent or solvent mixture. Subsequently, by means of recrystallization, the desired form of the crystalline compound of the present invention is obtained, where preferably seed crystals of the desired form, such as form B or form C, are added. Solvents or solvent mixtures which can be used are all of the aforementioned solvents. Particular preference is given to ethanol, ethyl acetate, 2-propanol and mixtures thereof. Optionally, a suitable amount of water can be added.

EXAMPLES

X-Ray Powder Diffraction

Powder diffractograms were measured on a Bruker D8 Advance powder diffractometer with a goniometer radius of 217.5 mm using copper Kα radiation. This instrument operates in reflections Bragg-Brentano geometry at an anode voltage of 40 kV and a current of 40 mA, using a variable divergence screen. The Bruker D8 instrument is equipped with a LynxEye detector, the active observation window being adjusted to 3°. The step size was 0.02° and the equivalent accumulation time was 37 seconds per step. The samples were prepared without further treatment on circular silicon single-crystal supports with a depth of 0.1 mm and a diameter of 12 mm. The samples were rotated during measurement at 0.5 revolutions per second. The measurement error is about ±0.1° 2θ.

Raman Spectroscopy

Fourier Transformation Raman spectroscopy was carried out using a Bruker RFS100 which has a Nd:YAG laser with a wavelength of 1064 nm for the excitation. The laser power used was 300 mW. The instrument used is equipped with a liquid nitrogen-cooled germanium detector. Ca. 3 mg of the measurement sample are pressed into a small aluminum support and this support is inserted into the spectrometer measurement chamber. For the recording of spectra, 64 accumulations with a resolution of 2.0 $cm^{-1}$ in the range 100-3500 $cm^{-1}$ wave numbers were measured. The measurement error is about ±1 $cm^{-1}$.

Water Vapor Adsorption Measurements

Dynamic water vapor adsorption measurements were carried out using an SPS11-100n instrument, manufactured by "Projekt Messtechnik" in Ulm, Germany. For this, ca. 20 mg of the sample were weighed into an aluminum support and this was inserted into the measurement chamber of the instrument. The sample was then subjected to preselected relative humidities in accordance with a defined program, the change in mass being determined over the time. The following measurement program was used: 50% r.h. constant for two hours, then changing the relative humidity to 0% r.h., then changing the relative humidity to 96% r.h., constant at 96% r.h. for four hours and then changing the relative humidity to 50% r.h. and then constant at 50% r.h. for one hour. The change rates set were in each case 5% per hour.

$^1$H-NMR Spectroscopy $^1$H-NMR spectroscopy was carried out on a Bruker DPX300 instrument. Sitagliptin fumarate samples were usually measured in DMSO-$d_6$.

Preparation of the Crystalline Sitagliptin Fumarate Compounds

Example 1

500.7 mg (1.23 mmol) of sitagliptin free base and 142.8 mg (1.23 mmol) of fumaric acid were stirred into 50 ml of ethyl methyl ketone at room temperature. After one hour, the resulting clear solution was heated by means of a hot-air blast and cooled in an ultrasound bath. Concentration of the solution to ca. 40 ml using a stream of $N_2$ led to a precipitation, which was filtered. Seed crystals from the first precipitation were added to the mother liquor, which was stored at room temperature. The suspension obtained was filtered and the white solid was dried for 30 min at about 3 mbar. Using X-ray powder diffraction, the typical powder diagram of form A is found; this is shown in FIG. 1. The most important reflections are mentioned in table 2 below. The $^1$H-NMR spectroscopy of the same sample reveals a molar ratio of sitagliptin to fumaric acid of 1:1.

TABLE 2

Powder X-ray data for form A

| °2θ angle | d value [Å] | Relative intensities (qualitative) |
|---|---|---|
| 6.8 | 12.9 | w |
| 8.6 | 10.3 | w |
| 15.8 | 5.59 | m |
| 17.2 | 5.15 | m |
| 18.9 | 4.69 | m |
| 20.7 | 4.30 | vs |
| 25.4 | 3.50 | s |
| 27.7 | 3.22 | s | w stands for weak, m for medium, s for strong and vs for very strong

Figure 4:
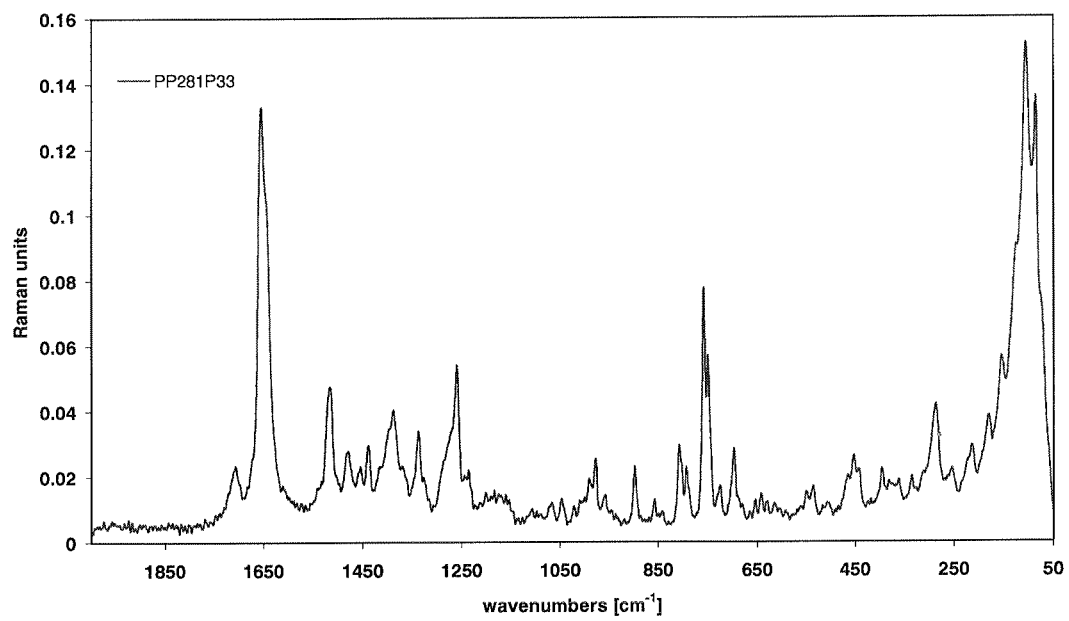
FIG. 4 is a Raman spectrum of form A.

The Raman-spectroscopic investigation of the resulting product reveals the characteristic Raman spectrum of form A, which is shown in FIG. 4. The most important peaks are given in table 3.

TABLE 3

Raman spectrum of form A

| Wave number [$cm^{-1}$] | Relative intensity (qualitative) |
|---|---|
| 3083 | m |
| 3034 | m |
| 3019 | m |
| 2940 | s |
| 1707 | w |
| 1655 | vs |
| 1516 | m |
| 1479 | w |
| 1439 | w |
| 1389 | m |
| 1338 | m |
| 1260 | m |
| 979 | w |
| 899 | w |
| 807 | w |
| 791 | w |
| 756 | s |
| 748 | m |
| 697 | w |
| 537 | w |
| 453 | w |
| 396 | w |
| 288 | m |
| 181 | m |
| 104 | vs |
| 85 | vs | w stands for weak, m for medium, s for strong and vs for very strong

Example 2

2.0 g (4.91 mmol) of sitagliptin free base and 571 mg (4.92 mmol) of fumaric acid were stirred in 150 ml of ethyl methyl ketone at room temperature for 1 h. After adding a further 60 ml of ethyl methyl ketone, the cloudy solution was heated by means of a hot-air blast. After cooling to room temperature, seed crystals of the sitagliptin fumarate were added to the now clear solution and the solution was stored at room temperature with exclusion of light. After three days, the resulting suspension was filtered and the white solid was dried for 2 hours at about 3 mbar (yield: 1.35 g). The material obtained was characterized by means of Raman spectroscopy, $^1$H-NMR spectroscopy, elemental analysis, thermogravimetry, coupled with infrared spectroscopy, and also with dynamic water vapor sorption measurement. The thermogravimetry coupled with FT-IR spectroscopy reveals that the minimally dried sample comprises only just ca. 0.5% water and a small amount of ethyl methyl ketone. $^1$H-NMR spectroscopy reveals a ratio of sitagliptin to fumaric acid of 1:1. Taking into consideration the small contents of water and residual solvent, this ratio is in agreement with the result of the elemental analysis, which revealed the following values: C=45.5%, H=3.5%, N=13.2%, O=15.6% and F=21.6%. The Raman spectroscopy shows the typical Raman spectrum of form A. The dynamic water vapor sorption shows that form A, even at high relative humidities, absorbs only a small amount of water.

Example 3

67.5 mg of sitagliptin fumarate from example 2 were dissolved in 4 ml of ethanol/ethyl acetate (1:1 v/v) at 65° C. The clear solution was cooled to 20° C. at 0.5° C./h, during which a suspension was formed. After filtration, the white solid was dried for 15 hours at 3 mbar. The resulting product was analyzed by means of Raman spectroscopy, X-ray powder diffraction and $^1$H-NMR spectroscopy. The $^1$H-NMR spectroscopy shows a molar ratio of sitagliptin to fumaric acid of 1:0.8. Raman spectroscopy and X-ray powder diffraction show the characteristic spectrum or diffractogram, respectively which are typical of sitagliptin form B.

FIG. 2 shows a powder diffractogram of form B. The most important reflections are mentioned in table 4 below.

TABLE 4

Powder X-ray data for form B

| °2θ angle | d value [Å] | Relative intensities (qualitative) |
|---|---|---|
| 6.2 | 14.1 | s |
| 7.2 | 12.3 | s |
| 12.6 | 7.0 | s |
| 14.4 | 6.1 | s |
| 19.2 | 4.62 | vs |
| 22.0 | 4.03 | vs |
| 25.3 | 3.51 | vs | w stands for weak, m for medium, s for strong and vs for very strong

Example 4

46.3 mg of sitagliptin fumarate from example 2 was dissolved in 12.4 ml of 2-propanol at 65° C. The clear solution was cooled to 20° C. at 0.5° C./h. Since no precipitation was observed, the solution was stirred for 2.5 hours at 5° C. The gel-like suspension formed was stirred for 7 days at room temperature and then filtered. The solid was dried for 15 hours at about 3 mbar. The resulting product was analyzed by means of Raman spectroscopy, X-ray powder diffraction and $^1$H-NMR spectroscopy. The $^1$H-NMR spectroscopy shows a molar ratio of sitagliptin to fumaric acid of 1:0.7. Raman spectroscopy and X-ray powder diffraction show the characteristic spectrum or diffractogram, respectively, which are typical of sitagliptin form C.

FIG. 3 shows a powder diffractogram of form C. The most important reflection are mentioned in table 5 below.

TABLE 5

Powder X-ray data for form C

| °2θ angle | d value [Å] | Relative intensities (qualitative) |
|---|---|---|
| 4.8 | 18.3 | m |
| 6.4 | 13.9 | s |
| 7.3 | 12.2 | w |
| 7.7 | 11.4 | s |
| 14.2 | 6.2 | s |
| 17.7 | 5.02 | m |
| 19.4 | 4.56 | vs |
| 22.1 | 4.03 | vs |
| 25.6 | 3.47 | vs | w stands for weak, m for medium, s for strong and vs for very strong

The invention claimed is:

1. A crystalline compound of 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine (INN: Sitagliptin) of formula 1

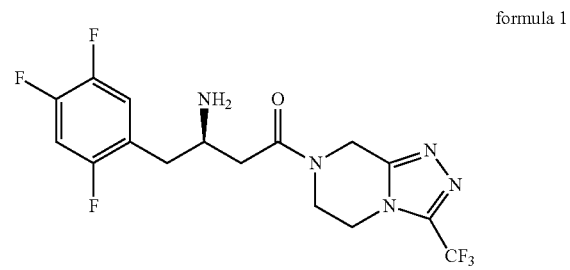 [SMILES: N[C@@H](CC(=O)N1CCn2c(nnc2C(F)(F)F)C1)Cc1cc(F)c(F)cc1F]

formula 1 with fumaric acid thereof, where the molar ratio of the compound of formula 1 to fumaric acid is 1:0.95 to 1:1.05, which has, by means of x-ray powder diffractometry (XRPD) d values (Å) at 12.9 (w), 10.3 (w), 5.15 (m) and 4.30 (vs), which is subsequently referred to as form A.

2. The crystalline compound of claim 1, which has, by means of X-ray powder diffractometry (XRPD) d values (Å) at 12.9 (w), 10.3 (w), 5.15(m), 4.69 (m), 4.30 (vs), 3.50 (s), 3.22 (s).

3. A pharmaceutical composition comprising the crystalline compound of claim 1 and a pharmaceutically acceptable excipient.

4. A method of treating Type II diabetes comprising administering to a subject in need thereof an effective amount of the pharmaceutical composition of claim 3.

5. A method for producing the crystalline compound of claim 1, the method comprising the steps of:
    a) providing a solution of 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine (INN: Sitagliptin) of formula 1,
    b) adding fumaric acid to the solution in step a),
    c) optionally concentrating the composition obtained after step b) and/or optionally adding non-solvent for lowering the solubility of the crystalline compound, and
    d) removing the solid obtained; wherein the crystalline compound of formula 1(Sitagliptin) and fumaric acid are stirred into 2-butanone (methyl ethyl ketone) or acetonitrile and the molar ratio of Sitagliptin to fumaric acid is 1:1 ±0.1.

6. The method of claim 5, wherein the molar ratio of the dissolved compound of formula 1 in step a) to the fumaric acid in step b) is 1:0.95 to 1:1.05.

7. The method of claim 5, wherein the fumaric acid in step b) is added as a solid to the solution in step a), or the fumaric acid in step b) is added as a solution in a solvent to the solution in step a).

* * * * *